US00PP28426P3

(12) United States Plant Patent
Ammerlaan

(10) Patent No.: US PP28,426 P3
(45) Date of Patent: Sep. 19, 2017

(54) *CRASSULA* PLANT NAMED 'CRASMADA'

(50) Latin Name: ***Crassula ovata* (Mill.) Druce.**
Varietal Denomination: Crasmada

(71) Applicant: Johannes Hendrikus Adrianus Ammerlaan, Bleiswijk (NL)

(72) Inventor: Johannes Hendrikus Adrianus Ammerlaan, Bleiswijk (NL)

(73) Assignee: Ovata B.V., Bleiswijk (NL)

( * ) Notice: Subject to any disclaimer, the term of this patent is extended or adjusted under 35 U.S.C. 154(b) by 108 days.

(21) Appl. No.: 14/757,034

(22) Filed: Nov. 10, 2015

(65) Prior Publication Data

US 2016/0157407 P1 Jun. 2, 2016

(30) Foreign Application Priority Data

Nov. 27, 2014 (QZ) ..... PBR 2014/3155

(51) Int. Cl.
*A01H 5/12* (2006.01)

(52) U.S. Cl.
USPC ..... Plt./373

(58) Field of Classification Search
USPC ..... Plt./373
See application file for complete search history.

*Primary Examiner* — Anne Grunberg
(74) *Attorney, Agent, or Firm* — Samuel R. McCoy, Jr.

(57) ABSTRACT

A new and distinct *Crassula* cultivar named 'Crasmada' which is characterized by the combination of dark green foliage, incurved margin deflection, an upward curling of the distal portion of the lamina, large foliage, a large plant size, and the stability of all characteristics from generation to generation. The new variety is a *Crassula*, typically produced as an indoor ornamental plant.

2 Drawing Sheets

Latin name of the genus and species: The Latin name of the genus and species of the novel variety disclosed herein is *Crassula ovata* (Mill.) Druce.

Variety denomination: The inventive variety of *Crassula* disclosed herein has been given the variety denomination 'Crasmada'.

CROSS REFERENCE TO RELATED APPLICATIONS

This application claims priority to the Community Plant Variety Rights application number 2014/3155, filed Nov. 27, 2014, which is herein incorporated by reference.

BACKGROUND OF THE INVENTION

Parentage: The *Crassula* variety 'Crasmada' originated as a naturally occurring, partial-plant mutation of *Crassula* 'Minova Magic' (unpatented in the United States, Community Plant Breeder's Rights No. EU37471), a variety developed and owned by the inventor. The inventor of 'Crasmada' is a commercial ornamental plant producer and regularly discovers branch and leaf mutations of *Crassula* 'Minova Magic' at his greenhouse operation in Bleiswijk, The Netherlands. For said mutations which seem to exhibit commercial potential, cuttings are taken to produce trial plants which are subsequently grown for evaluation. Several of such mutations were isolated for evaluation based on dark green coloration of the leaf, in combination with other desirable characteristics.

The variety now called 'Crasmada' was initially discovered in 2011 as one such branch mutation of 'Minova Magic'. At the time of discovery, cuttings were taken and the resulting plants were evaluated at the inventor's greenhouse. After further evaluation it was determined that the candidate's dark green foliage, incurved margin deflection, and upwardly curled leaf would prove favorable for commercial marketability. The new variety was given the breeder denomination 'Crasmada'.

Asexual Reproduction: 'Crasmada' was first asexually propagated by stem cuttings in October of 2011 at a greenhouse in Bleiswijk, The Netherlands and has since been vegetatively propagated through six additional generation. Through subsequent generations, the unique features of this cultivar are stable and reproduced true to type.

SUMMARY OF THE INVENTION

The cultivar 'Crasmada' has not been observed under all possible environmental conditions and the phenotype may vary somewhat with variations in environment such as temperature, day length, and light intensity, without, however, any variance in genotype. The following traits have been repeatedly observed and are determined to be the unique characteristics of 'Crasmada'. These characteristics in combination distinguish 'Crasmada' as a new and distinct *Crassula* cultivar:

1. *Crassula* 'Crasmada' exhibits dark green foliage; and
2. *Crassula* 'Crasmada' exhibits incurved margin deflection; and
3. *Crassula* 'Crasmada' exhibits an upward curling of the distal portion of the lamina; and,
4. *Crassula* 'Crasmada' exhibits large foliage; and
5. *Crassula* 'Crasmada' exhibits a large overall plant size.

BOTANICAL DESCRIPTION OF THE PLANT

Figure 1:
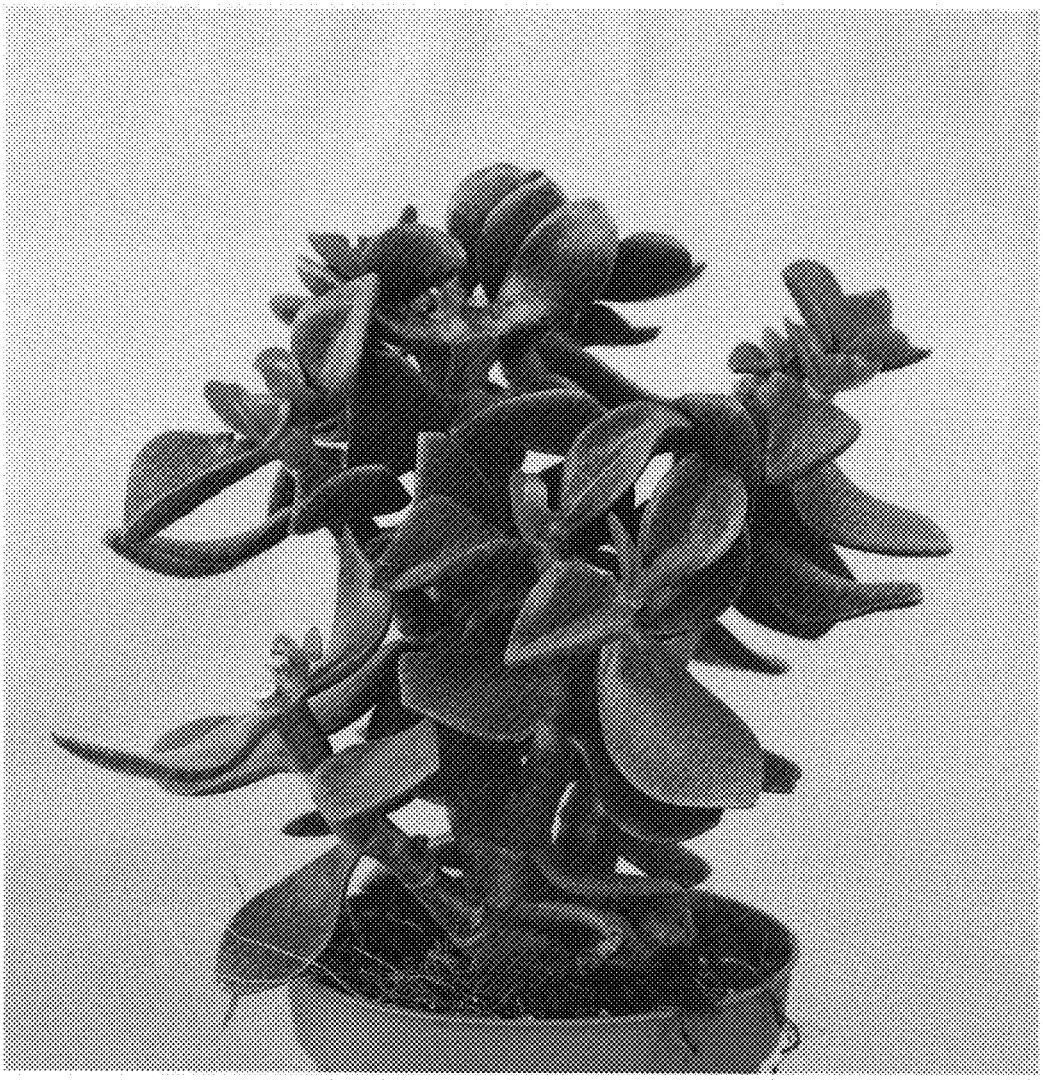
FIG. 1 illustrates, as nearly true as it is reasonably possible to make the same in color photographs of this type, an exemplary plant of 'Crasmada' grown in a grown in a commercial greenhouse in Bleiswijk, The Netherlands. This plant is approximately 12 months old, shown planted in a 12 cm container.
Figure 2:
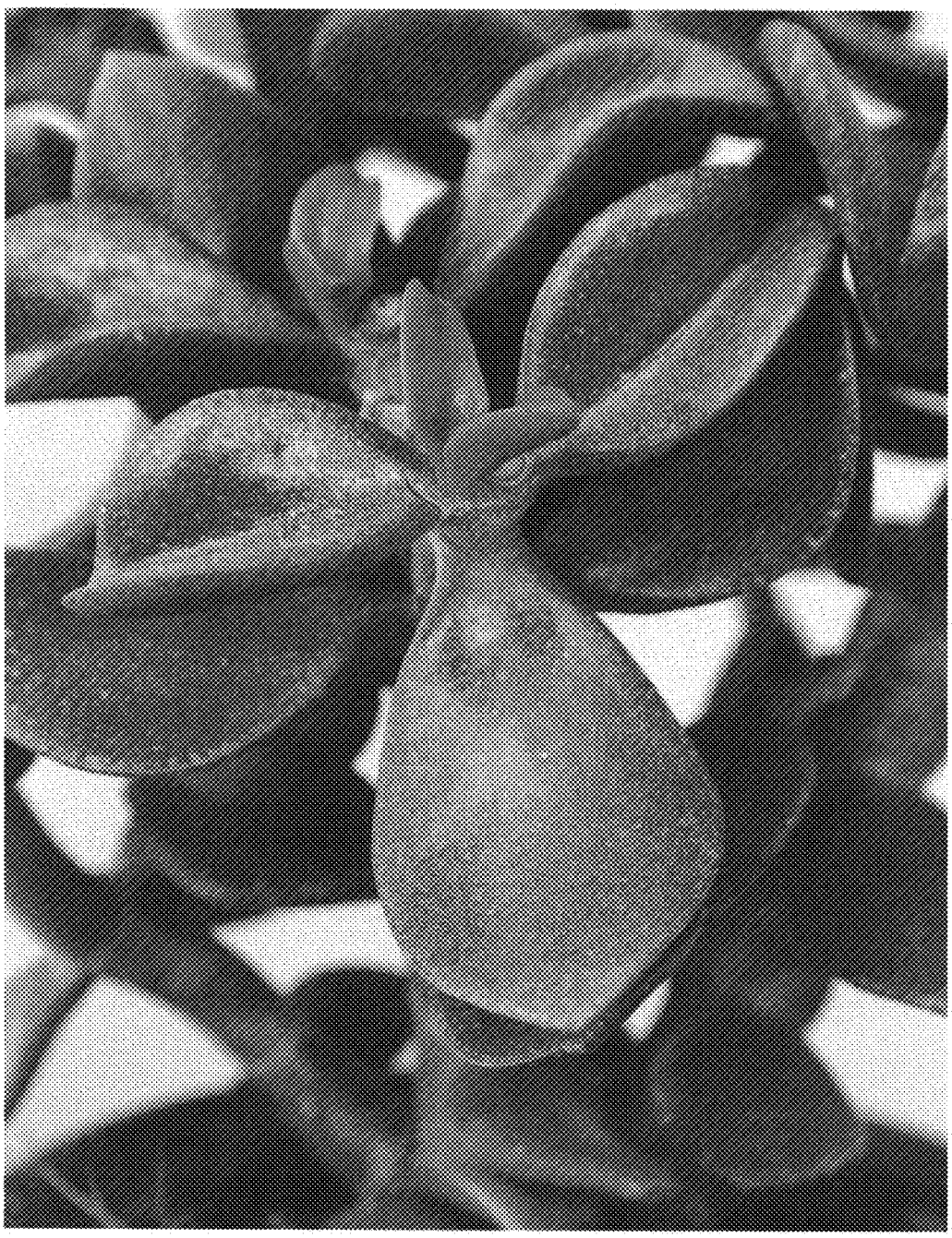
FIG. 2 illustrates, as nearly true as it is reasonably possible to make the same in color photographs of this type, the typical foliage of 'Crasmada'.

The following observations and measurements describe a twelve month-old 'Crasmada' plant grown in 12 cm nursery pots at a commercial greenhouse in Bleiswijk, The Netherlands. The plants were grown in full sun to semi-shade. Plants were maintained with a standard fertility program for plants of this type and regularly watered with overhead irrigation as well as through use of ebb-and-flow hydroponic greenhouse benches. No chemical pest measures were taken.

Those skilled in the art will appreciate that certain characteristics will vary with older or, conversely, with younger plants. 'Crasmada' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climactic and cultural conditions. Color notations are based on *The Royal Horticultural Society Colour Chart*, The Royal Horticultural Society, London, 2015 (sixth edition).

A botanical description of 'Crasmada' and comparisons with other varieties of *Crassula* are provided below.

Plant description:

*Growth habit*.—Broad upright, overall shape obovate.

*Average height*.—19.1 cm from the soil level to the highest leaf.

*Plant spread*.—Average of 18.0 cm.

*Growth rate*.—Moderate; approximately 2 cm per month.

*Propagation type*.—Stem cuttings.

*Time to initiate roots*.—Approximately 14 days to initiate roots at temperatures ranging from 15 to 20 degrees Celsius.

*Time to produce a rooted cutting*.—Approximately 6 weeks to produce a rooted cutting.

*Disease resistance*.—Similar to other *Crassula* varieties.

*Temperature tolerances*.—Tolerates temperatures ranging from approximately 12 to 45 degrees Celsius.

Root system:

*General*.—Thin; moderately fibrous.

*Texture*.—Not fleshy.

*Color*.—Greyed-Orange RHS 166C.

Stem:

*General branching habit*.—Moderately free branching; apical pruning will induce branching.

*Quantity of lateral branches*.—Approximately 7.

*Length of lateral branches*.—Approximately 7.6 cm.

*Diameter of lateral branches*.—Approximately 1.1 cm.

*Internode length*.—Approximately 1.9 cm.

*Texture*.—Glabrous and very slight glossiness.

*Stength*.—Strong.

*Color*.—Juvenile stems are green near RHS 137B, and mature stems are greyed-brown, near RHS 199B to 199D.

Foliage:

*Arrangement*.—Opposite.

*Abundance; density*.—8 paired leaves per lateral branch; approximately 60 leaves per plant.

*Lamina*.—Dimensions — 5.2 cm long (including the leaf sheath) and 3.1 cm wide. Thickness — Approximately 0.5 cm. Shape of blade — Obovate; slightly twisted with distal one-third to one-half of lamina curled upward. Aspect — Leaves are 90 degrees to the stem. Apex — Broad acute. Base — Cuneate. Margin — Entire; incurved deflection. Texture of top surface — Glabrous, glossy. Texture of bottom surface — Glabrous, glossy. Color — Juvenile foliage, adaxial surface — Green to yellow-green, in between near RHS 143B and 144A. Juvenile foliage, abaxial surface — Green near RHS 143B. Mature foliage, adaxial surface — Green to yellow-green, near RHS 147A; densely and finely dotted with lenticels, colored greyed-green near RHS 195A and 195B. Mature foliage, abaxial surface — Green to yellow-green, near RHS 147A; densely and finely dotted with lenticels, colored greyed-green near RHS 195A and 195B. Venation — No veins are visible.

*Petiole*.—No petioles present, leaves sessile.

Inflorescence: No flowering has been observed to date.

COMPARISONS WITH THE PARENT PLANTS

'Crasmada' is similar in many horticultural characteristics to its parent plant, *Crassula* 'Minova Magic'. However 'Crasmada' differs from 'Minova Magic' in the following characteristics:

1. The foliage color of 'Crasmada' is dark green, whereas the foliage color of 'Minova Magic' is a lighter green color.
2. 'Crasmada' exhibits larger foliage when compared to the foliage of 'Minova Magic'.
3. 'Crasmada' exhibits a growth habit that is less obtuse and more pointed when compared to the leaf apex of 'Minova Magic'.
4. 'Crasmada' exhibits a more pronounced upward curling of the distal portion of the lamina when compared to that of 'Minova Magic'.
5. 'Crasmada' exhibits a larger overall plant size when compared to 'Minova Magic'.

COMPARISONS WITH THE MOST SIMILAR VARIETY KNOWN TO THE INVENTOR

'Crasmada' is similar in may horticultural characteristics to *Crassula* 'Magical Tree' (not patented). However 'Crasmada' differs from 'Magical Tree' in the following characteristics:

1. The foliage color of 'Crasmada' is dark green, whereas the foliage color of 'Magical Tree' is a lighter green color.
2. The leaf margin of 'Crasmada' is dark green whereas 'Magical Tree' exhibits leaf margins suffused with reddish brown.
3. The growth habit of 'Crasmada' is less upright compared to that of 'Magical Tree'.
4. 'Magical Tree' is more densely foliaged than 'Crasmada'.

That which is claimed is:

1. A new and distinct variety of *Crassula* plant named 'Crasmada', substantially as described and illustrated herein.

* * * * *